United States Patent [19]

Fischer et al.

[11] Patent Number: 5,116,836

[45] Date of Patent: May 26, 1992

[54] 3-PHENYL-PYRROLIDINE-2,4-DIONE DERIVATIVES HAVING PESTICIDAL ACTIVITY

[75] Inventors: Reiner Fischer, Monheim; Hermann Hagemann, Leverkusen; Andreas Krebs, Odenthal-Holz; Albrecht Marhold; Hans-Joachim Santel, both of Leverkusen; Robert R. Schmidt; Klaus Lürssen, both of Bergisch-Gladbach, all of Fed. Rep. of Germany; Benedikt Becker, Steinmannhof, Italy; Wilhelm Stendel, Wuppertal; Christoph Erdelen, Leichlingen, both of Fed. Rep. of Germany

[73] Assignee: Bayer Aktiengesellschaft, Leverkusen, Fed. Rep. of Germany

[21] Appl. No.: 567,872

[22] Filed: Aug. 15, 1990

[30] Foreign Application Priority Data

Sep. 1, 1989 [DE] Fed. Rep. of Germany ....... 3929087

[51] Int. Cl.$^5$ .................... C07D 279/08; A61K 31/54
[52] U.S. Cl. .................... 514/224.2; 544/47; 514/368; 548/166; 548/178; 71/90; 71/91
[58] Field of Search .................... 544/47; 514/224.2

[56] References Cited

U.S. PATENT DOCUMENTS 4,139,364  2/1979  Wolf ........................................ 71/92

FOREIGN PATENT DOCUMENTS 0090312  5/1983  European Pat. Off. .
0262399  6/1988  European Pat. Off. .

OTHER PUBLICATIONS

CA 109(13):110249g (1988) Prep of 4-hydroxy 2(5H)--thiophenones and pynolidones . . . scavengers.
Chem. Pharm. Bull., vol. 15 (1967) 1120-1123.
Liebigs. Ann. Chem. 1985, 1095-1098.

Primary Examiner—Cecilia Shen
Assistant Examiner—Jyothsna Venkat
Attorney, Agent, or Firm—Sprung Horn Kramer & Woods

[57] ABSTRACT

Novel 3-aryl-pyrrolidine 2,4-dione derivatives of the formula

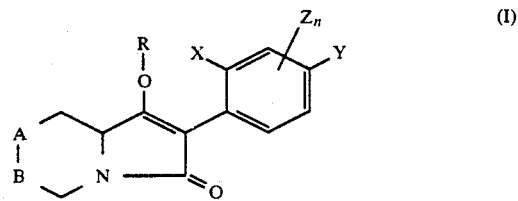

having pesticidal activity.

6 Claims, No Drawings

3-PHENYL-PYRROLIDINE-2,4-DIONE DERIVATIVES HAVING PESTICIDAL ACTIVITY

This invention relates to new 3-aryl-pyrrolidine-2,4-dione derivatives, to a number of processes for their preparation and to their use as herbicides, insecticides and acaricides.

Pharmaceutical properties of 3-acyl-pyrrolidine-2,4-diones have previously been described (S. Suzuki et. al. Chem. Pharm. bull. 15 1120 (1967)) Furthermore, N-phenyl-pyrrolidine-2,4-diones have been synthesized by R. Schmierer and H. Mildenberger Liebigs Ann. Chem. 1985 1095. A biological activity of these compounds has not been described.

Compounds having a similar structure (3-arylpyrrolidine-2,4-diones) are disclosed in EP-A 0,262,399, wherein, however, no herbicidal, fungicidal, antimycotic, tickicidal, insecticidal or acaricidal activity has been disclosed.

New 3-aryl-pyrrolidine-2,4-dione derivatives have now been found which are represented by the formula (I)

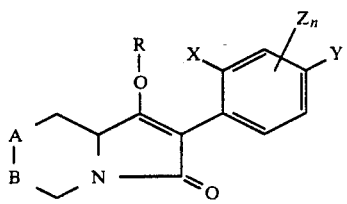

in which
A—B represents —S—CH$_2$—, —SO—CH$_2$—, —SO$_2$CH$_2$—, —CH$_2$—S—, —CH$_2$SO—, —CH$_2$SO$_2$—, —S—, —SO— or —SO$_2$—,
X represents alkyl, halogen or alkoxy,
Y represents hydrogen, alkyl, halogen, alkoxy or halogenoalkyl,
Z represents alkyl, halogen or alkoxy,
n represents a number from 0-3,
R represents hydrogen, E or the groups —CO—R$^1$ or —CO—O—R$^2$, in which
  E represents a metal cation equivalent or an ammonium ion,
  R$^1$ represents alkyl, alkenyl, alkoxyalkyl, alkylthioalkyl, polyalkoxyalkyl and optionally substituted cycloalkyl, which can be interrupted by heteroatoms, which are optionally substituted by halogen, optionally substituted phenyl, optionally substituted phenylalkyl, substituted hetaryl, substituted phenoxyalkyl and substituted hetaryloxyalkyl and
  R$^2$ represents alkyl, cycloalkyl, alkenyl, alkoxyalkyl, polyalkoxyalkyl and optionally substituted phenyl which are optionally substituted by halogen,
and the enantiomerically pure forms of compounds of the formula (I).

The following subgroups may be defined in the following:
(Ia): compounds of the formula (I) in which R=hydrogen,
(Ib): compounds of the formula (I) in which R=COR$^1$,
(Ic): compounds of the formula (I) in which R=COOR$^2$,
(Id): compounds of the formula (I) in which R=a metal ion equivalent or an ammonium ion.
(Ie): compounds of the formula (I) in which A—B=—SO—CH$_2$—, —CH$_2$—SO or —SO—,
(If): compounds of the formula (I) in which A—B=—SO$_2$—CH$_2$—, —CH$_2$—SO$_2$— or —SO$_2$—.

Furthermore, it has been found that 3-arylpyrrolidine-2,4-diones or their enols of the formula (Ia)

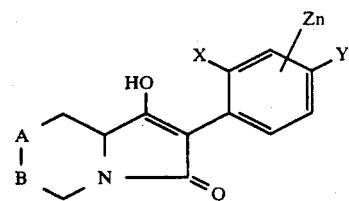

are obtained when
(A) N-acylamino acid esters of the formula (II)

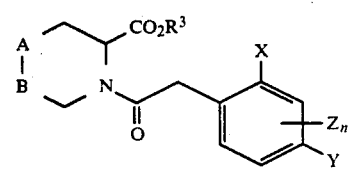

in which
A, B, X, Y, Z and n have the abovementioned meanings and
R$^3$ represents alkyl, are intramolecularly condensed in the presence of a diluent and in the presence of a base.

(B) In addition, it has been found that compounds of the formula (Ib)

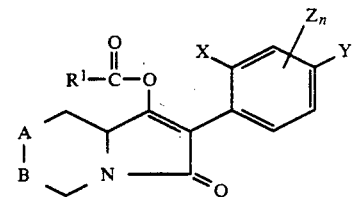

are obtained when compounds of the formula (Ia)

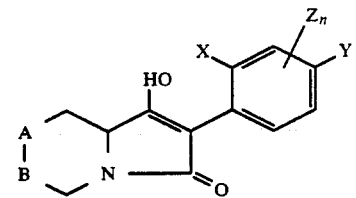

in which
A, B, X, Y, Z and n have the abovementioned meanings,
α) are reacted with acid halides of the general formula (III)

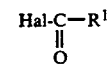

in which
R$^1$ has the abovementioned meaning
and

Hal represents halogen, in particular chlorine and bromine, if appropriate in the presence of a diluent and if appropriate in the presence of an acid-binding agent, or β) with carboxylic acid anhydrides of the general formula (IV)

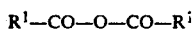
$R^1$—CO—O—CO—$R^1$ (IV)

in which $R^1$ has the abovementioned meaning, if appropriate in the presence of a diluent and if appropriate in the presence of an acid-binding agent.

(C) It has further been found that compounds of the formula (Ic)

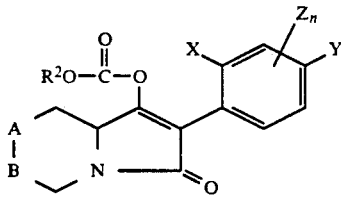
(Ic)

are obtained when compounds of the formula (Ia)

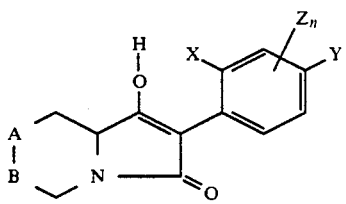
(Ia)

in which

A, B, X, Y, Z and n have the abovementioned meanings, are reacted with chloroformic acid esters of the general formula (V)

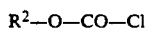
$R^2$—O—CO—Cl (V)

in which $R^2$ has the abovementioned meaning, if appropriate in the presence of a diluent and if appropriate in the presence of an acid-binding agent.

(D) It has furthermore been found that compounds of the formula (Id)

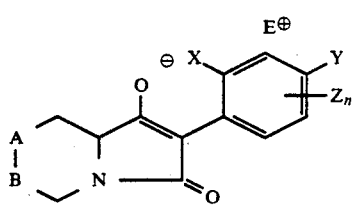
(Id)

in which

A, B, X, Y, Z, E and n have the abovementioned meanings, are obtained when compounds of the formula (Ia)

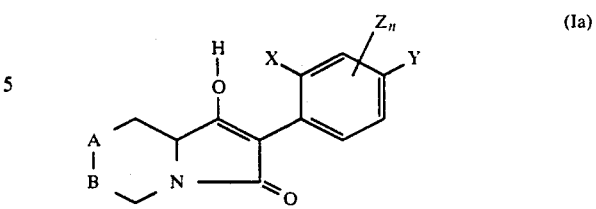
(Ia)

in which

A, B, X, Y, Z and n have the abovementioned meanings, are reacted with metal hydroxides or amines of the general formulae (VIII) and (IX)

$Me_sOH_t$ (VIII)

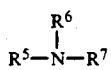
$R^5$—N—$R^7$ (IX)
  |
  $R^6$ in which

Me represents mono- or divalent metal ions, s and t represent the number 1 and 2 and $R^5$, $R^6$ and $R^7$ independently of one another represent hydrogen and alkyl, if appropriate in the presence of a diluent.

(E) It has further been found that compounds of the formula (Ie)

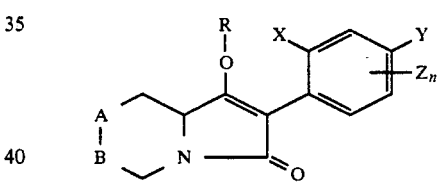
(Ie)

in which

A, B, R, X, Y, Z and n have the abovementioned meanings, are obtained when compounds of the formula (Ia)-(Ic)

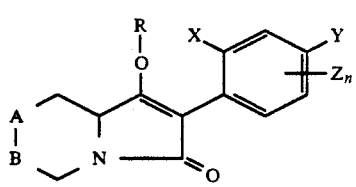
(Ia)-(Ic)

in which

R, X, Y, Z and n have the abovementioned meanings and

A—B represents —S—$CH_2$—, —$CH_2$—S— or —S—, are reacted with approximately equimolar amounts of an oxidizing agent, if appropriate in the presence of a diluent.

(F) It has additionally been found that compounds of the formula (If)

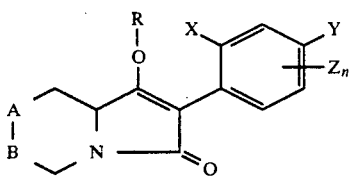

(If)

in which A, B, R, X, Y, Z and n have the abovementioned meanings, are obtained when compounds of the formula (Ia)–(Ic)

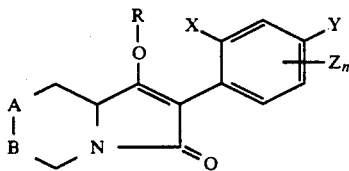

(Ia)-(Ic)

in which

R, X, Y, Z and n have the abovementioned meanings and

A—B represents —S—CH$_2$—, —CH$_2$—S— or —S—, are reacted with double the equimolar amounts of an oxidizing agent, if appropriate in the presence of a diluent.

Surprisingly, it has been found that the new 3-aryl-pyrrolidine-2,4-diones of the formula (I) are distinguished by outstanding herbicidal, insecticidal, antimycotic and acaricidal actions.

Condensed 1,5-alkylene-3-aryl-pyrrolidine-2,4-diones and their corresponding enol esters of the formula (I) are preferred in which A—B represents —S—CH$_2$—, —SO—CH$_2$—, —SO$_2$—CH$_2$—, —CH$_2$—S—, —CH$_2$—SO—, —CH$_2$—SO$_2$—, —S—, —SO— or —SO$_2$—, X represents C$_1$–C$_6$-alkyl, halogen or C$_1$–C$_6$-alkoxy, Y represents hydrogen, C$_1$–C$_6$-alkyl, halogen, C$_1$–C$_6$-alkoxy or C$_1$–C$_3$-halogenoalkyl, Z represents C$_1$–C$_6$-alkyl, halogen or C$_1$–C$_6$-alkoxy, n represents a number from 0–3, R represents hydrogen (Ia) or the groups of the formula —CO—R$^1$ (Ib), —CO—O—R$^2$ (Ic)

or

E (Id)

in which

E represents a metal cation equivalent or an ammonium ion,

R$^1$ represents C$_1$–C$_{20}$-alkyl, C$_2$–C$_{20}$-alkenyl, C$_1$–C$_8$-alkoxy-C$_1$–C$_8$-alkyl, C$_1$–C$_8$-alkylthio-C$_1$–C$_8$-alkyl, C$_1$–C$_8$-polyalkoxy-C$_2$–C$_8$-alkyl and cycloalkyl having 3–8 ring atoms, which may be interrupted by oxygen and/or sulphur, which are optionally substituted by halogen, represents phenyl which is optionally substituted by halogen, nitro, C$_1$–C$_6$-alkyl, C$_1$–C$_6$-alkoxy, C$_1$–C$_6$-halogenoalkyl or C$_1$–C$_6$-halogenoalkoxy; represents phenyl-C$_1$–C$_6$-alkyl which is optionally substituted by halogen, C$_1$–C$_6$-alkyl, C$_1$–C$_6$-alkoxy, C$_1$–C$_6$-halogenoalkyl or C$_1$–C$_6$-halogenoalkoxy, represents hetaryl optionally substituted by halogen and C$_1$–C$_6$-alkyl, represents phenoxy-C$_1$–C$_6$-alkyl optionally substituted by halogen and C$_1$–C$_6$-alkyl, or represents hetaryloxy-C$_1$–C$_6$-alkyl optionally substituted by halogen, amino and C$_1$–C$_6$-alkyl, R$^2$ represents C$_1$–C$_{20}$-alkyl, C$_2$–C$_{20}$-alkenyl, C$_1$–C$_8$-alkoxy-C$_2$–C$_8$-alkyl or C$_1$–C$_8$-polyalkoxy-C$_2$–C$_8$-alkyl which are optionally substituted by halogen, or represents phenyl optionally substituted by halogen, nitro, C$_1$–C$_6$-alkyl, C$_1$–C$_6$-alkoxy or C$_1$–C$_6$-halogenoalkyl, and the enantiomerically pure forms of compounds of the formula (I).

Compounds of the formula (I) are particularly preferred in which

A—B represents —S—CH$_2$—, —SO—CH$_2$—, —SO$_2$—CH$_2$—, —CH$_2$—S—, —CH$_2$—SO—, —CH$_2$—SO$_2$—, —S—, —SO— or —SO$_2$—, X represents C$_1$–C$_4$-alkyl, halogen or C$_1$–C$_4$-alkoxy, Y represents hydrogen, C$_1$–C$_6$-alkyl, halogen, C$_1$–C$_4$-alkoxy, or C$_1$–C$_2$-halogenoalkyl, Z represents C$_1$–C$_4$-alkyl, halogen or C$_1$–C$_4$-alkoxy, n represents a number from 0–3, R represents hydrogen (Ia) or the groups of the formula —CO—R$^1$ (Ib), —CO—O—R$^2$ (Ic)

or

E (Id)

in which

E represents a metal cation equivalent or an ammonium ion,

R$^1$ represents C$_1$–C$_{16}$-alkyl, C$_2$–C$_{16}$-alkenyl, C$_1$–C$_6$-alkoxy-C$_1$–C$_6$-alkyl, C$_1$–C$_6$-alkylthio-C$_1$–C$_6$-alkyl, C$_1$–C$_6$-polyalkoxy-C$_2$–C$_6$-alkyl and cycloalkyl having 3–7 ring atoms, which can be interrupted by 1–2 oxygen and/or sulphur atoms, which are optionally substituted by halogen, represents phenyl optionally substituted by halogen, nitro, C$_1$–C$_4$-alkyl, C$_1$–C$_4$-alkoxy, C$_1$–C$_3$-halogenoalkyl or C$_1$–C$_3$-halogenoalkoxy, represents phenyl-C$_1$–C$_4$-alkyl optionally substituted by halogen, C$_1$–C$_4$-alkyl, C$_1$–C$_4$-alkoxy, C$_1$–C$_3$-halogenoalkyl or C$_1$–C$_3$-halogenoalkoxy, represents hetaryl optionally substituted by halogen and C$_1$–C$_6$-alkyl, optionally represents phenoxy-C$_1$–C$_5$-alkyl substituted by halogen and C$_1$–C$_4$-alkyl, or represents hetaryloxy-C$_1$–C$_5$-alkyl optionally substituted by halogen, amino and C$_1$–C$_4$-alkyl, R$^2$ represents C$_1$–C$_6$-alkyl, C$_2$–C$_{16}$-alkenyl, C$_1$–C$_{16}$-alkoxy-C$_2$–C$_6$-alkyl or C$_1$–C$_6$-polyalkoxy-C$_2$–C$_6$-alkyl which are optionally substituted by halogen, or represents phenyl optionally substituted by halogen, nitro, C$_1$–C$_4$-alkyl, C$_1$–C$_3$-alkoxy or C$_1$–C$_3$-halogenoalkyl, and the enantiomerically pure forms of compounds of the formula (I).

Compounds of the formula (I) are very particularly preferred in which

A—B represents —S—CH$_2$—, —SO—CH$_2$—, —SO$_2$—CH$_2$—, —CH$_2$—S—, —CH$_2$—SO—, —CH$_2$SO$_2$—, —S—, —SO— or —SO$_2$, X represents methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, chlorine, bromine, methoxy, ethoxy and trifluoromethyl, Z represents methyl, ethyl, i-propyl, butyl, i-butyl, tert.-butyl, chlorine, bromine, methoxy and ethoxy, n represents a number from 0–3, R represents hydrogen (Ia) or the groups of the formula —CO—R$^1$ (Ib), —CO—O—R$^2$ (Ic)

or

E (Id)

in which

E represents a metal cation equivalent or an ammonium ion,

R$^1$ represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxyl-$C_2$–$C_4$-alkyl and cycloalkyl having 3–6 ring atoms, which can be interrupted by 1–2 oxygen and/or sulphur atoms, which are optionally substituted by fluorine or chlorine, represents phenyl optionally substituted by fluorine, chlorine, bromine, methyl, ethyl, propyl, i-propyl, methoxy, ethoxy, trifluoromethyl, trifluoromethoxy or nitro, represents phenyl-$C_1$–$C_3$-alkyl optionally substituted by fluorine, chlorine, bromine, methyl, ethyl, propyl, i-propyl, methoxy, ethoxy, trifluoromethyl or trifluoromethoxy, represents pyridyl, pyrimidyl, thiazolyl and pyrazolyl which are optionally substituted by fluorine, chlorine, bromine, methyl or ethyl, represents phenoxy-$C_1$–$C_4$-alkyl optionally substituted by fluorine, chlorine, methyl or ethyl, or represents pyridyloxy-$C_1$–$C_4$-alkyl, pyrimidyloxy-$C_1$–$C_4$-alkyl and thiazolyloxy-$C_1$–$C_4$-alkyl which are optionally substituted by fluorine, chlorine, amino, methyl or ethyl, R$^2$ represents $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl which are optionally substituted by fluorine or chlorine, or represents phenyl optionally substituted by fluorine, chlorine, nitro, methyl, ethyl, propyl, i-propyl, methoxy, ethoxy or trifluoromethyl, and the enantiomerically pure forms of compounds of the formula I. If ethyl N-(2,6-dichlorophenylacetyl)-1,4-thiomorpholine-3-carboxylate is used according to process (A), the course of the process according to the invention can be represented by the following equation:

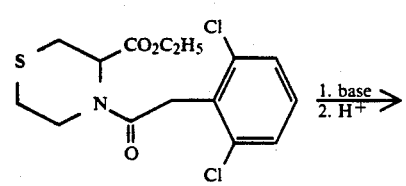

If 3-(2,4,6-trimethylphenyl)-1,5-ethylmercaptomethyl-pyrrolidine-2,4-dione and pivaloyl chloride are used as starting material according to process (B) (variant α), the course of the process according to the invention can be represented by the following equation:

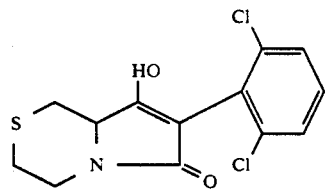

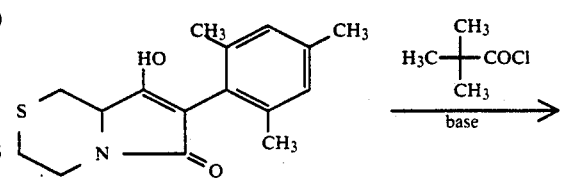

If 3-(2,4,5-trimethylphenyl)-1,5-methylmercaptoethyl-pyrrolidine-2,4-dione and acetic anhydride are used according to process (B) (variant β), the course of the process according to the invention can be represented by the following equation:

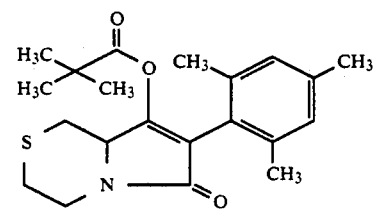

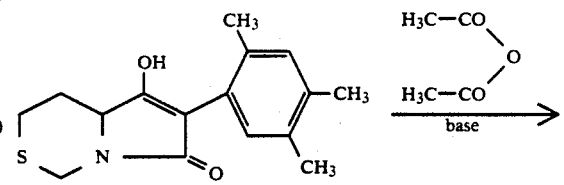

If 3-(2,4-dichlorophenyl)-1,5-methylmercaptoethyl-pyrrolidine-2,4-dione and ethoxyethyl chloroformate are used according to process (C) the course of the process according to the invention can be represented by the following equation:

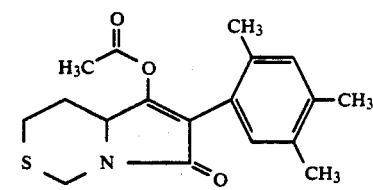

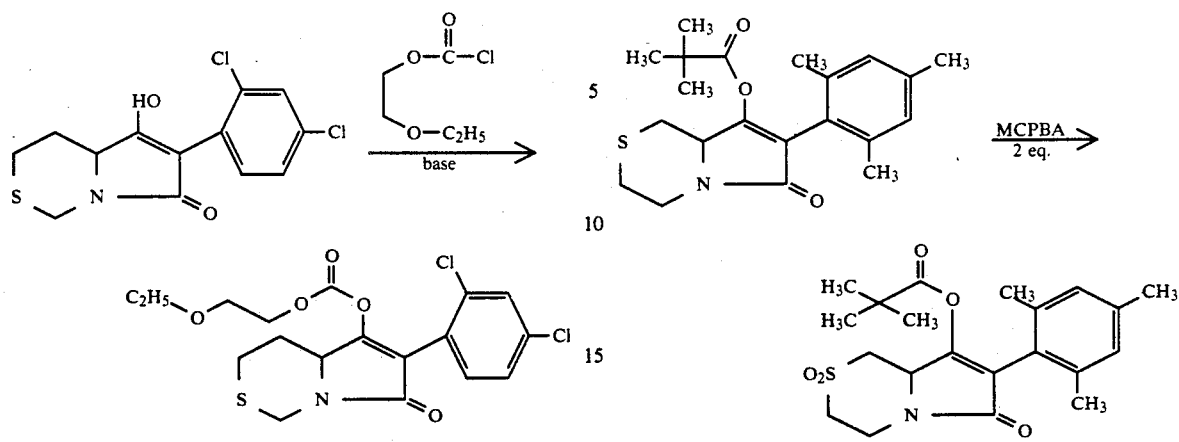

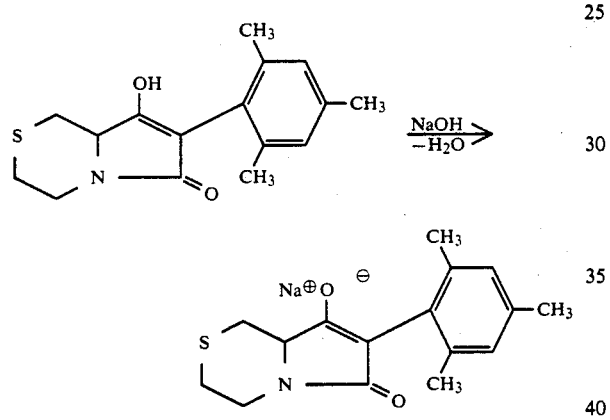

If 3-(2,1,6-trimethylphenyl-1,5-ethylmercaptomethyl-pyrrolidine-2,4-dione and NaOH are used according to process (D), the course of the process according to the invention can be represented by the following equation:

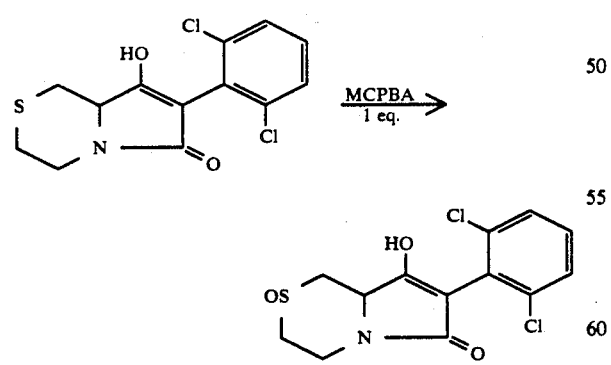

If 3-(2,6-dichlorophenyl)-1,5-ethylmercaptomethyl-pyrrolidine-2,4-dione and an equimolar amount of m-chloroperbenzoic acid are used according to process (E), the course of the process according to the invention can be represented by the following equation:

If 4-(pivaloyloxy)-3-(2,4,6-trimethylphenyl)-1,5-ethylmercaptomethyl-3-pyrrolin-2-one and double the equimolar amount of m-chloroperbenzoic acid is used according to process (F), the course of the process according to the invention can be represented by the following equation:

The compounds of the formula (II)

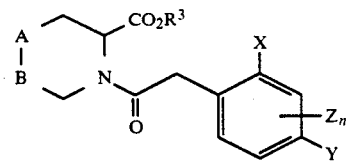 (II)

in which

A, B, X, Y, Z, n and $R^3$ have the abovementioned meanings, required as starting materials in the above process (A) are not known, but can be prepared in a simple manner according to methods which are known in principle. Thus, for example, acylamino acid esters of the formula (II) are obtained when a) amino acid esters of the formula (VI)

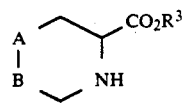 (VI)

in which

A and B have the abovementioned meanings and
$R^3$ represents alkyl, are acylated with phenylacetic acid halides of the formula (VII)

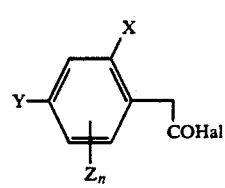 (VII)

in which

X, Y, Z and n have the abovementioned meanings and Hal represents chlorine or bromine, (general method described in: Chem. Reviews 52 237–416 (1953);

or when b) acylamino acids of the formula (IIa)

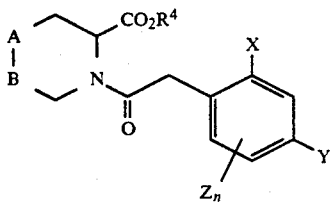

in which

A, B, X, Y, Z and n have the abovementioned meanings and

R⁴ represents hydrogen, are esterified (general method described in: Chem. Ind. (London) 1568 (1968)).

Compounds of the formula (IIa) are obtainable, for example, from the phenylacetic acid halides of formula (VIa)

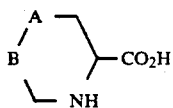

in which

A and B have the abovementioned meanings, according to Schotten-Baumann (Organikum 9th edition 44) (1970) VEB Deutscher Verlag der Wissenschaften, Berlin).

Compounds of the formula (VI) and (VIa) are known compounds and can be prepared in a simple manner.

The following compounds of the formula (II) may be mentioned by way of example:

1) Ethyl N-(2,4-dichlorophenylacetyl)-1,4-thiomorpholine-3-carboxylate
2) Ethyl N-(2,6-dichlorophenylacetyl)-1,4-thiomorpholine-3-carboxylate
3) Ethyl N-(2,4,6-trichlorophenylacetyl)-1,4-thiomorpholine-3-carboxylate
4) Ethyl N-(2,4-dimethylphenylacetyl)-1,4-thiomorpholine-3-carboxylate
5) N-(2,6-Dimethylphenylacetyl)-1,4-thiomorpholine-3-carboxylic acid ester
6) N-(2,4,6-Trimethylphenylacetyl)-1,4-thiomorpholine-3-carboxylic acid ester
7) Ethyl N-(2-chloro-6-fluorophenylacetyl)-1,4-thiomorpholine-3-carboxylate
8) Ethyl N-(2,6-dichloro-4-trifluoromethylphenylacetyl)-1,4-thiomorpholine-3-carboxylate
9) Ethyl N-(2,4-dichlorophenylacetyl)-1,3-thiomorpholine-4-carboxylate
10) Ethyl N-(2,6-dichlorophenylacetyl)-1,3-thiomorpholine-4-carboxylate
11) Ethyl N-(2,4,6-trichlorophenylacetyl)-1,3-thiomorpholine-4-carboxylate
12) Ethyl N-(2,4-dimethylphenylacetyl)-1,3-thiomorpholine-4-carboxylate
13) Ethyl N-(2,6-dimethylphenylacetyl)-1,3-thiomorpholine-4-carboxylate
14) Ethyl N-(2,4,6-trimethylphenylacetyl)-1,3-thiomorpholine-4-carboxylate
15) Ethyl N-(2-chloro-6-fluorophenylacetyl)-1,3-thiomorpholine-4-carboxylate
16) Ethyl N-(2,6-dichloro-4-trifluoromethylphenylacetyl)-1,3-thiomorpholine-4-carboxylate
17) Ethyl N-(2,4-dichlorophenylacetyl)-thiazolidine-4-carboxylate
18) Ethyl N-(2,6-dichlorophenylacetyl)-thiazolidine-4-carboxylate
19) Ethyl N-(2,4,6-trichlorophenylacetyl)-thiazolidine-4-carboxylate
20) Ethyl N-(2,4-dimethylphenylacetyl)-thiazolidine-4-carboxylate
21) Ethyl N-(2,6-dimethylphenylacetyl)-thiazolidine-4-carboxylate
22) Ethyl N-(2,4,6-trimethylphenylacetyl)-thiazolidine-4-carboxylate
23) Ethyl N-(2-chloro-6-fluorophenylacetyl)-thiazolidine-4-carboxylate
24) Ethyl N-(2,6-dichloro-4-trifluoromethylphenylacetyl)-4-thiazolidine-carboxylate.

The reaction temperatures can be varied within a relatively wide range when carrying out process (A) according to the invention. In general, the reaction is carried out at temperatures between 0° C. and 250° C., preferably between 50° C. and 150° C.

Process (A) according to the invention is in general carried out under normal pressure.

When carrying out process (A) according to the invention, the reactants of the formulae (II) and the deprotonating bases are in general employed in approximately equimolar amounts. However, it is also possible to use one or the other component in a relatively large excess (up to 3 moles).

Process (A) is characterized in that compounds of the formula (II) in which X, Y, Z, m, n and R³ have the abovementioned meanings are subjected to an intramolecular condensation in the presence of bases.

Diluents which can be employed in process (A) according to the invention are all customary inert organic solvents. Those which may be preferably used are hydrocarbons, such as cyclohexane, toluene and xylene, furthermore ethers, such as dibutyl ether, tetrahydrofuran, dioxane, glycol dimethyl ether and diglycol dimethyl ether, and additionally polar solvents, such as dimethyl sulphoxide, sulpholane, dimethylformamide and N-methyl-pyrrolidone.

Deprotonating agents which can be employed when carrying out process (A) according to the invention are all customary proton acceptors. Those which can preferably be used are oxides, hydroxides and carbonates of alkali metals and alkaline earth metals, such as sodium hydroxide, potassium hydroxide, magnesium oxide, calcium oxide, sodium carbonate, potassium carbonate and calcium carbonate, which can also be employed in the presence of phase transfer catalysts such as, for example, triethylbenzylammonium chloride, tetrabutylammonium bromide, Adogen 464=(methyltrialkyl($C_8$–$C_{10}$)ammonium chloride) or TDA=(tris-(methoxyethoxyethyl)-amine). Amides and hydrides of alkali metals and alkaline earth metals, such as sodium amide, sodium hydride and calcium hydride, and additionally also alkali metal alkoxides, such as sodium methoxide, sodium ethoxide and potassium tert.-butoxide can furthermore be employed.

The process (Bα) is characterized in that compounds of the formula (Ia) are reacted with carboxylic acid halides of the formula (III).

Diluents which can be employed in process (Bα) according to the invention when using the acid halides are all solvents which are inert to these compounds. Those which may preferably be used are hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, moreover carboxylic acid esters, such as ethyl acetate, and also strongly polar solvents, such as dimethyl sulphoxide and sulpholane. If the stability to hydrolysis of the acid halide permits it, the reaction can also be carried out in the presence of water.

If the corresponding carboxylic acid halides are used, possible acid-binding agents for the reaction by process (Bα) according to the invention are all customary acid acceptors. Those which are preferably utilizable are tertiary amines, such as triethylamine, pyridine, DABCO, DBU, DBA, Hünig base and N,N-dimethyl-aniline, furthermore alkaline earth metal oxides, such as magnesium oxide and calcium oxide, and additionally carbonates of alkali metals and alkaline earth metals, such as sodium carbonate, potassium carbonate and calcium carbonate.

The reaction temperatures may also be varied within a relatively wide range in process (Bα) according to the invention even when using carboxylic acid halides. In general, the reaction is carried out at temperatures between $-20°$ C. and $+150°$ C., preferably between 0° C. and 100° C.

When carrying out process (Bα) according to the invention, the starting materials of the formula (Ia) and the carboxylic acid halide of the formula (III) are in general employed in approximately equivalent amounts. However, it is also possible to employ the carboxylic acid anhydride in a relatively large excess (up to 5 times the molar amount). Working up is carried out by customary methods.

Process (Bβ) is characterized in that compounds of the formula (Ia) are reacted with carboxylic acid hydrides of the formula (IV).

If carboxylic acid anhydrides are used as reactants of the formula (IV) in process (Bβ) according to the invention, diluents which can be used are preferably those diluents which are also preferable when using acid halides. Otherwise, a carboxylic acid hydride employed in excess may also simultaneously function as a diluent.

The reaction temperatures can be varied within a relatively wide range when carrying out process (Bβ) according to the invention even when using carboxylic acid anhydrides. In general, the reaction is carried out at temperatures between $-20°$ C. and $+150°$ C., preferably between 0° C. and 100° C.

When carrying out the process according to the invention, the starting materials of the formula (Ia) and the carboxylic acid anhydride of the formula (IV) are in general used in approximately equivalent amounts. However, it is also possible to employ the carboxylic acid anhydride in a relatively large excess (up to 5 times the molar amount). Working up is carried out by customary methods.

In general, a procedure is used in which the diluent and excess carboxylic acid anhydride and also the carboxylic acid formed are removed by distillation or by washing with an organic solvent or with water.

Process (C) is characterized in that compounds of the formula (Ia) are reacted with chloroformic acid esters of the formula (V).

If the corresponding chloroformic acid esters are used, possible acid-binding agents for the reaction by process (C) according to the invention are all customary acid acceptors. Those which may be preferably used are tertiary amines, such as triethylamine, pyridine, DABCO, DBC, DBA, Hünig base and N,N-dimethyl-aniline, furthermore alkaline earth metal oxides, such as magnesium oxide and calcium oxide, and additionally carbonates of alkali metals and alkaline earth metals, such as sodium carbonate, potassium carbonate and calcium carbonate.

Diluents which can be used in process (C) according to the invention when using the chloroformic acid esters are all solvents which are inert to these compounds. Those which may be preferably used are hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, additionally ketones, such as acetone and methyl isopropyl ketone, furthermore ethers, such as diethyl ether, tetrahydrofuran and dioxane, moreover carboxylic acid esters, such as ethyl acetate, and also strongly polar solvents, such as dimethyl sulphoxide and sulpholane.

When using the chloroformic acid esters as carboxylic acid derivatives of the formula (V), the reaction temperatures can be varied within a relatively wide range when carrying out process (C) according to the invention. If the reaction is carried out in the presence of a diluent and an acid-binding agent, the reaction temperatures are in general between $-20°$ C. and $+100°$ C., preferably between 0° C. and 50° C.

Process (C) according to the invention is in general carried out under normal pressure.

When carrying out process (C) according to the invention, the starting materials of the formula (Ia) and the corresponding chloroformic acid ester of the formula (V) are in general used in approximately equivalent amounts. However, it is also possible to employ one or the other component amount). Working up is then carried out by customary methods. In general, a procedure is used in which deposmethods. In general, a procedure is used in which deposited salts are removed and the remaining reaction mixture is concentrated by stripping off the diluent.

Process (D) is characterized in that compounds of the formula (Ia) are reacted with acetal hydroxides (VIII) or amines (IX).

Diluents which can be used in the process according to the invention are preferably ethers such as tetrahydrofuran, dioxane, diethyl ether or else alcohols such as methanol, ethanol, isopropanol, and also water. Process (D) according to the invention is in general carried out under normal pressure. The reaction temperatures are in general between $-20°$ C. and 100° C., preferably between 0° C. and 50° C.

When carrying out process (D) according to the invention, the starting materials of the formula (Ia) and (IX) are in general used in approximately equimolar amounts. However, it is also possible to employ one component or the other in a relatively large excess (up to 2 times the molar amount). In general, a procedure is used in which the reaction mixture is concentrated by stripping off the diluent.

When carrying out process (E) according to the invention, the starting materials of the formula (Ia) to (Ic) and the corresponding oxidizing agent are employed in approximately equimolar amounts. Working up is carried out by customary methods.

Suitable oxidizing agents for process (E) according to the invention are all sulphur-oxidizing reagents, for example halogen such as chlorine and bromine and their aqueous solutions, alkali metal peroxides such as sodium peroxide and potassium peroxide, salts of oxyhalic acids such as potassium chlorate, potassium bromate, sodium periodate and sodium perborate, furthermore inorganic persalts such as potassium permanganate, potassium peroxodisulphate and potassium peroxomonosulphate, but also $H_2O_2$ in the presence of transition metal salts such as sodium tungstate and ammonium molybdate. Organic peroxides such as tert.-butyl hydroperoxide and also organic peracids such as peracetic acid, perpropionic acid and m-chloroperbenzoic acid (MCPBA) may furthermore be used.

Diluents which may be used in process (E) according to the invention are all solvents which are inert to these compounds. Those which may be preferably used are hydrocarbons such as benzine, benzene, toluene, xylene and tetralin, furthermore halogenated hydrocarbons such as methylene chloride, chloroform, chlorobenzene and dichlorobenzene, additionally organic acids such as acetic acid and propionic acid, and water.

If the reaction is carried out in the presence of a diluent, the reaction temperatures can be varied within a relatively wide range when carrying out process (E) according to the invention. In general, the reaction temperatures are between $-30°$ C. and $+150°$ C., preferably between $0°$ C. and $100°$ C.

Process (E) according to the invention is in general carried out under normal pressure.

When carrying out process (F) according to the invention, the starting materials of the formula (Ia) to (Ic) and the corresponding oxidizing agent are employed in approximately double the equimolar amounts. However, it is also possible to employ the oxidizing agent in a relatively large excess (up to 4 times the molar amount). Working up is carried out by customary methods.

Suitable oxidizing agents for process (F) according to the invention are all sulphur-oxidizing reagents, for example halogen such as chlorine and bromine and their aqueous solutions, alkali metal peroxides such as sodium peroxide and potassium peroxide, salts of oxyhalic acids such as potassium chlorate, potassium bromate, sodium periodate and sodium perborate, furthermore inorganic persalts such as potassium permanganate, potassium peroxodisulphate and potassium peroxomonosulphate, and also $H_2O_2$ in the presence of transition metal salts such as sodium tungstate and ammonium molybdate. Organic peroxides such as tert.-butyl hydroperoxide and also organic peracids such as peracetic acid, perpropionic acid and m-chloroperbenzoic acid (MCPBA) may furthermore be used.

Diluents which can be employed in process (F) according to the invention are all solvents inert to these compounds. Those which may be preferably used are hydrocarbons such as benzine, benzene, toluene, xylene and tetralin, furthermore halogented hydrocarbons such as methylene chloride, chloroform, chlorobenzene and dichlorobenzene, additionally organic acids such as acetic acid and propionic acid, and water.

If the reaction is carried out in the presence of a diluent, the reaction temperatures can be varied within a relatively wide range when carrying out process (F) according to the invention. In general the reaction temperatures are between $-30°$ C. and $+150°$ C., preferably between $0°$ C. and $100°$ C.

Process (F) according to the invention is in general carried out under normal pressure.

EXAMPLE 1

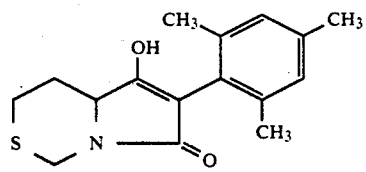

5.17 g (0.17 mol) of sodium hydride are initially introduced into 90 ml of absolute (abs.) toluene. 43 g (about 0.128 mol) of ethyl N-(2,4,6-trimethylphenylacetyl)-1,3-thiomorpholine-4-carboxylate, dissolved in 130 ml of abs. toluene, are added dropwise under reflux. After refluxing for 3 h, EtOH is added dropwise with ice bath cooling until the evolution of $H_2$ is complete. The mixture is concentrated in vacuo on a rotary evaporator, the residue is taken up in water and acidified at $0°$ to $10°$ C. with conc. HCl, and the crude product is filtered off with suction and dried at $70°$ C. in vacuo over $P_2O_5$. Purification is carried out by boiling with $CHCl_3$/MTB ether/n-hexane.

Yield: 32.06 g (86.5 % of theory) m.p. $294°$ C.

EXAMPLE 2

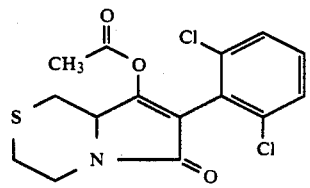

6.32 g (20 mmol) of 3-(2,6-dichlorophenyl)-1,5-ethylthiomethylpyrrolidine-2,4-dione are suspended in 50 ml of tert.-butyl methyl ether (MTB ether), and 1.63 ml (20 mmol) of abs. pyridine and 3.4 ml (20 mmol) of ethyldiisopropylamine are added. 1.5 ml (20 mmol) of acetyl chloride, dissolved in 5 ml of MTB ether, are added dropwise at $0°$ to $10°$ C., the mixture is subsequently stirred at room temperature for 30 min., the precipitate is filtered off, the filtrate is concentrated in vacuo, the residue is purified by column chromatography on silica gel using cyclohexane/ethyl acetate 1:1 and the product is crystallized out from n-hexane. Yield: 3.7 g (51.6 % of theory) m.p. $112°$ C.

EXAMPLE 3

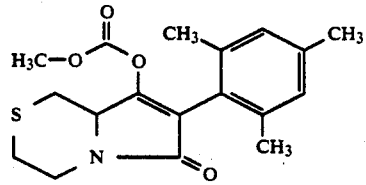

5.78 g (20 mmol) of 3-(2,4,6-trimethyl)-1,5-ethylthiomethylpyrrolidine-2,4-dione are suspended in 50 ml of MTB ether, and 1.63 ml (20 mmol) of abs. pyridine and 3.4 ml (20 mmol) of ethyl diisopropylamine are added. 1.55 ml (20 mmol) of methyl chloroformate, dissolved in 5 ml of MTB ether, are added dropwise at $0°$ to $10°$ C., the mixture is subsequently stirred at room temperature for 30 min., the precipitate is filtered off, the filtrate is concentrated in vacuo and the residue is purified by column chromatography on silica gel using cyclohexane/ethyl acetate 1:1. 5.26 g (75.7 % of theory) of a colorless oil having a purity, determined by gas chromatography, of 95 % are obtained.

$^1$H-NMR (200 MHz, CDCl$_3$): δ=2.13, 2.14 (2 s, 6 H, Ar—2—CH$_3$, Ar—6—CH$_3$), 2.28 (s, 3 H, Ar—4—CH$_3$), 2.43-2.8 (m, 3 H, CH$_2$—S—CH$_2$), 2.97-3.25 (m, 2 H), 4.57 (ABq, 1 H), 4.7 ("dt", 1 H, N—CH—C=) 6.9 (s, 2 H, Ar—3 H, 6-H).

EXAMPLE 4

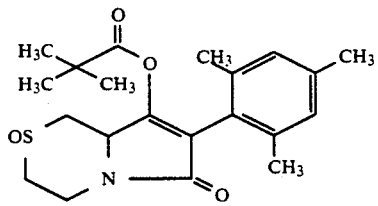

7.47 g (20 mmol) of 4-pivaloyloxy-3-(2,4,6-trimethylphenyl)-1,5-ethylmercaptomethyl-3-pyrrolin-2-one are dissolved in 60 ml of chloroform and a solution of 4.2 g (20 mmol) of m-chloroperbenzoic acid in 50 ml of chloroform is added dropwise at 0° to 5° C. After stirring at 0° C. for 1 h, the solution is washed twice with NaHCO$_3$ solution, dried and concentrated in vacuo, and the residue is recrystallized from methylene chloride/n-hexane.

Yield: 2.95 g (38% of theory) m.p. 217° C.

EXAMPLE 5

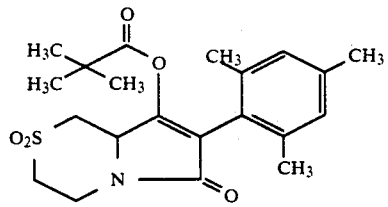

7.47 g (20 mmol) of 4-pivaloyloxy-3-(2,4,6-trimethylphenyl)-1,5-ethylmercaptomethyl-3-pyrrolin-2-one are dissolved in 60 ml of chloroform and a solution of 9.24 g (44 mmol) of m-chloroperbenzoic acid in 100 ml of chloroform is added dropwise at 0° to 5° C. After stirring at 0° C. for 1 h, the solution is washed twice with NaHCO$_3$ solution, dried and concentrated in vacuo, and the residue is recrystallized from methylene chloride/n-hexane.

Yield: 5.7 g (70.3% of theory) m.p. 235° C.

The 3-aryl-pyrrolidine-2,4-dione derivatives of the formula (Ia) to (Ie) shown according to formula in the following Tables 1 to 3 can be obtained in a corresponding manner to the Preparation Examples and according to the general instructions for preparation.

TABLE 1 (Ia)

| No. | A—B | X | Y | Z$_n$ | m.p. °C. |
|---|---|---|---|---|---|
| 6 | —S— | Cl | Cl | H | 220 |
| 7 | —SO— | Cl | Cl | H | |
| 8 | —SO$_2$— | Cl | Cl | H | |
| 9 | —S—CH$_2$— | Cl | Cl | H | 225 |
| 10 | —SO—CH$_2$— | Cl | Cl | H | |
| 11 | —SO$_2$—CH$_2$— | Cl | Cl | H | |
| 12 | —CH$_2$—S— | Cl | Cl | H | 205 |
| 13 | —CH$_2$—SO— | Cl | Cl | H | |
| 14 | —CH$_2$—SO$_2$— | Cl | Cl | H | |
| 15 | —S— | Cl | H | 6-Cl | |
| 16 | —SO— | Cl | H | 6-Cl | |
| 17 | —SO$_2$— | Cl | H | 6-Cl | |
| 18 | —S—CH$_2$— | Cl | H | 6-Cl | >230 |
| 19 | —SO—CH$_2$— | Cl | H | 6-Cl | |
| 20 | —SO$_2$—CH$_2$— | Cl | H | 6-Cl | |
| 21 | —CH$_2$—S— | Cl | H | 6-Cl | |
| 22 | —CH$_2$—SO— | Cl | H | 6-Cl | |
| 23 | —CH$_2$—SO$_2$— | Cl | H | 6-Cl | |
| 24 | —S— | CH$_3$ | CH$_3$ | 6-CH$_3$ | 221 |
| 25 | —SO— | CH$_3$ | CH$_3$ | 6-CH$_3$ | |
| 26 | —SO$_2$— | CH$_3$ | CH$_3$ | 6-CH$_3$ | |
| 27 | —S—CH$_2$— | CH$_3$ | CH$_3$ | 6-CH$_3$ | 231 |
| 28 | —SO—CH$_2$— | CH$_3$ | CH$_3$ | 6-CH$_3$ | |
| 29 | —SO$_2$—CH$_2$— | CH$_3$ | CH$_3$ | 6-CH$_3$ | |
| 30 | —CH$_2$—SO— | CH$_3$ | CH$_3$ | 6-CH$_3$ | |
| 31 | —CH$_2$—SO$_2$— | CH$_3$ | CH$_3$ | 6-CH$_3$ | |

TABLE 2 (Ib)

| No. | A—B | X | Y | Z$_n$ | R$^1$ | m.p. °C. |
|---|---|---|---|---|---|---|
| 32 | —S— | Cl | Cl | H | CH$_3$— | |
| 33 | —S— | Cl | Cl | H | (CH$_3$)$_3$C— | |
| 34 | —S— | Cl | Cl | H | (CH$_3$)$_2$CH—C(CH$_3$)$_2$— | oil |
| 35 | —SO— | Cl | Cl | H | (CH$_3$)$_3$C— | |
| 36 | —SO$_2$— | Cl | Cl | H | (CH$_3$)$_3$C— | |
| 37 | —S— | Cl | H | 6-Cl | CH$_3$— | |
| 38 | —S— | Cl | H | 6-Cl | (CH$_3$)$_3$C— | |
| 39 | —S— | CH$_3$ | CH$_3$ | 6-CH$_3$ | CH$_3$— | |
| 40 | —S— | CH$_3$ | CH$_3$ | 6-CH$_3$ | (CH$_3$)$_2$CH— | |
| 41 | —S— | CH$_3$ | CH$_3$ | 6-CH$_3$ | (CH$_3$)$_3$C— | |
| 42 | —S— | CH$_3$ | CH$_3$ | 6-CH$_3$ | (CH$_3$)$_2$CH—C(CH$_3$)$_2$— | |
| 43 | —SO— | CH$_3$ | CH$_3$ | 6-CH$_3$ | CH$_3$— | |
| 44 | —SO— | CH$_3$ | CH$_3$ | 6-CH$_3$ | (CH$_3$)$_3$C— | |
| 45 | —SO$_2$— | CH$_3$ | CH$_3$ | 6-CH$_3$ | CH$_3$— | |
| 46 | —SO$_2$— | CH$_3$ | CH$_3$ | 6-CH$_3$ | (CH$_3$)$_3$C— | |

TABLE 2-continued (Ib)

$$R^1-\overset{O}{\underset{}{C}}-O \quad \text{structure with } X, Y, Z_n, A, B$$

| No. | A—B | X | Y | $Z_n$ | $R^1$ | m.p. °C. |
|---|---|---|---|---|---|---|
| 47 | —S—CH$_2$— | Cl | Cl | H | CH$_3$— | |
| 48 | —S—CH$_2$— | Cl | Cl | H | (CH$_3$)$_3$C— | |
| 49 | —S—CH$_2$— | Cl | Cl | H | (CH$_3$)$_2$CH—(CH$_3$)$_2$C— | oil |
| 50 | —SO—CH$_2$— | Cl | Cl | H | (CH$_3$)$_3$C— | |
| 51 | —SO$_2$—CH$_2$— | Cl | Cl | H | (CH$_3$)$_3$C— | |
| 52 | —S—CH$_2$— | Cl | H | 6-Cl | (CH$_3$)$_2$CH— | |
| 53 | —S—CH$_2$— | Cl | H | 6-Cl | (CH$_3$)$_3$C— | oil |
| 54 | —S—CH$_2$ | Cl | H | 6-Cl | (CH$_3$)$_2$CH—(CH$_3$)$_2$C— | |
| 55 | —SO—CH$_2$ | Cl | H | 6-Cl | (CH$_3$)$_3$C— | |
| 56 | —SO$_2$—CH$_2$— | Cl | H | 6-Cl | (CH$_3$)$_3$C— | |
| 57 | —S—CH$_2$— | CH$_3$ | CH$_3$ | 6-CH$_3$ | CH$_3$— | glass |
| 58 | —S—CH$_2$— | CH$_3$ | CH$_3$ | 6-CH$_3$ | (CH$_3$)$_2$CH— | oil |
| 59 | —S—CH$_2$— | CH$_3$ | CH$_3$ | 6-CH$_3$ | (CH$_3$)$_3$C— | 110 |
| 60 | —S—CH$_2$— | CH$_3$ | CH$_3$ | 6-CH$_3$ | (CH$_3$)$_2$CH—(CH$_3$)$_2$C— | 74 |
| 61 | —S—CH$_2$— | CH$_3$ | CH$_3$ | 6-CH$_3$ | (CH$_3$)$_3$C—CH$_2$— | oil |
| 62 | —S—CH$_2$— | CH$_3$ | CH$_3$ | 6-CH$_3$ | Cl—CH$_2$—C(CH$_3$)$_2$— | 118 |
| 63 | —S—CH$_2$— | CH$_3$ | CH$_3$ | 6-CH$_3$ | CH$_3$O—CH$_2$—(CH$_3$)$_2$C— | oil |
| 64 | —S—CH$_2$— | CH$_3$ | CH$_3$ | 6-CH$_3$ | (CH$_3$)$_2$C=CH— | oil |
| 65 | —S—CH$_2$— | CH$_3$ | CH$_3$ | 6-CH$_3$ | 2,2-dimethyl-1,3-dioxolane group with CH$_3$ | 136 |
| 66 | —S—CH$_2$— | CH$_3$ | CH$_3$ | 6-CH$_3$ | 2-chlorophenyl | |
| 67 | —S—CH$_2$— | CH$_3$ | CH$_3$ | 6-CH$_3$ | 3-chlorophenyl | 130 |
| 68 | —S—CH$_2$— | CH$_3$ | CH$_3$ | 6-CH$_3$ | 4-chlorophenyl | 145 |
| 69 | —SO—CH$_2$— | CH$_3$ | CH$_3$ | 6-CH$_3$ | CH$_3$— | |
| 70 | —SO—CH$_2$— | CH$_3$ | CH$_3$ | 6-CH$_3$ | (CH$_3$)$_3$C—CH$_2$— | |
| 71 | —SO$_2$—CH$_2$— | CH$_3$ | CH$_3$ | 6-CH$_3$ | CH$_3$— | |
| 72 | —SO$_2$—CH$_2$— | CH$_3$ | CH$_3$ | 6-CH$_3$ | (CH$_3$)$_3$C—CH$_2$— | |
| 73 | —CH$_2$—S— | CH$_3$ | CH$_3$ | 6-CH$_3$ | CH$_3$— | 164 |
| 74 | —CH$_2$—S— | CH$_3$ | CH$_3$ | 6-CH$_3$ | (CH$_3$)$_2$CH— | 84 |
| 75 | —CH$_2$—S— | CH$_3$ | CH$_3$ | 6-CH$_3$ | (CH$_3$)$_3$C— | 123 |
| 76 | —CH$_2$—S— | CH$_3$ | CH$_3$ | 6-CH$_3$ | (CH$_3$)$_2$CH—(CH$_3$)$_2$C— | 113 |
| 77 | —CH$_2$—SO— | CH$_3$ | CH$_3$ | 6-CH$_3$ | CH$_3$— | |
| 78 | —CH$_2$—SO— | CH$_3$ | CH$_3$ | 6-CH$_3$ | (CH$_3$)$_3$C— | |
| 79 | —CH$_2$—S— | Cl | Cl | H | CH$_3$— | 139 |
| 80 | —CH$_2$—S— | Cl | Cl | H | (CH$_3$)$_2$CH—(CH$_3$)$_2$C— | 133 |

TABLE 3

(Ic)

| No. | A—B | X | Y | $Z_n$ | $R^2$ | m.p. °C. |
|---|---|---|---|---|---|---|
| 81 | —S— | Cl | Cl | H | $CH_3CH_2$— | |
| 82 | —S— | Cl | Cl | H | $(CH_3)_2CH$— | |
| 83 | —SO— | Cl | Cl | H | $CH_3CH_2$— | |
| 84 | —$SO_2$— | Cl | Cl | H | $CH_3CH_2$— | |
| 85 | —S—$CH_2$— | Cl | Cl | H | $CH_3CH_2$— | |
| 86 | —S—$CH_2$— | Cl | Cl | H | $(CH_3)_2CH$— | |
| 87 | —SO—$CH_2$— | Cl | Cl | H | $CH_3CH_2$— | |
| 88 | —$SO_2$—$CH_2$— | Cl | Cl | H | $CH_3CH_2$— | |
| 89 | —$CH_2$—S— | Cl | Cl | H | $CH_3CH_2$— | |
| 90 | —$CH_2$—S— | Cl | Cl | H | $(CH_3)_2CH$— | |
| 91 | —$CH_2$—SO— | Cl | Cl | H | $CH_3CH_2$— | |
| 92 | —$CH_2$—$SO_2$— | Cl | Cl | H | $CH_3CH_2$— | |
| 93 | —S— | Cl | H | 6-Cl | $CH_3CH_2$— | |
| 94 | —S— | Cl | H | 6-Cl | $(CH_3)_2CH$— | |
| 95 | —SO— | Cl | H | 6-Cl | $CH_3CH_2$— | |
| 96 | —$SO_2$— | Cl | H | 6-Cl | $CH_3CH_2$— | |
| 97 | —S—$CH_2$— | Cl | H | 6-Cl | $CH_3$— | |
| 98 | —S—$CH_2$— | Cl | H | 6-Cl | $CH_3CH_2$— | 95 |
| 99 | —S—$CH_2$— | Cl | H | 6-Cl | $(CH_3)_2CH$— | |
| 100 | —S—$CH_2$— | Cl | H | 6-Cl | $(CH_3)_2CH$—$CH_2$— | |
| 101 | —S—$CH_2$— | Cl | H | 6-Cl | $CH_3$\CH—/$C_2H_5$ | |
| 102 | —S—$CH_2$— | Cl | H | 6-Cl | $(CH_3)_3C$—$CH_2$— | |
| 103 | —SO—$CH_2$— | Cl | H | 6-Cl | $C_2H_5$— | |
| 104 | —SO—$CH_2$— | Cl | H | 6-Cl | $(CH_3)_2CH$— | |
| 105 | —$SO_2$—$CH_2$— | Cl | H | 6-Cl | $C_2H_5$— | |
| 106 | —$SO_2$—$CH_2$— | Cl | H | 6-Cl | $(CH_3)_2CH$— | |
| 107 | —$CH_2$—S— | Cl | H | 6-Cl | $C_2H_5$— | |
| 108 | —$CH_2$—S— | Cl | H | 6-Cl | $(CH_3)_2CH$— | |
| 109 | —$CH_2$—SO— | Cl | H | 6-Cl | $C_2H_5$— | |
| 110 | —$CH_2$—$SO_2$— | Cl | H | 6-Cl | $C_2H_5$— | |
| 111 | —S— | $CH_3$ | $CH_3$ | 6-$CH_3$ | $C_2H_5$— | |
| 112 | —S— | $CH_3$ | $CH_3$ | 6-$CH_3$ | $C_2H_5$— | |
| 113 | —SO— | $CH_3$ | $CH_3$ | 6-$CH_3$ | $C_2H_5$— | |
| 114 | —$SO_2$— | $CH_3$ | $CH_3$ | 6-$CH_3$ | $C_2H_5$— | |
| 115 | —S—$CH_2$— | $CH_3$ | $CH_3$ | 6-$CH_3$ | $(CH_3)_3C$— | |
| 116 | —S—$CH_2$— | $CH_3$ | $CH_3$ | 6-$CH_3$ | $(CH_3)_2CH$—$CH_2$— | oil |
| 117 | —S—$CH_2$— | $CH_3$ | $CH_3$ | 6-$CH_3$ | $CH_3$\CH—/$C_2H_5$ | oil |
| 118 | —S—$CH_2$— | $CH_3$ | $CH_3$ | 6-$CH_3$ | $(CH_3)_3C$—$CH_2$— | 95 |
| 119 | —S—$CH_2$— | $CH_3$ | $CH_3$ | 6-$CH_3$ | $C_2H_5$—O—$(CH_2)_2$— | oil |
| 120 | —S—$CH_2$— | $CH_3$ | $CH_3$ | 6-$CH_3$ | cyclohexyl | oil |
| 121 | —S—$CH_2$— | $CH_3$ | $CH_3$ | 6-$CH_3$ | phenyl | |
| 122 | —SO—$CH_2$— | $CH_3$ | $CH_3$ | 6-$CH_3$ | $C_2H_5$— | |
| 123 | —SO—$CH_2$— | $CH_3$ | $CH_3$ | 6-$CH_3$ | $(CH_3)_2CH$— | |
| 124 | —$SO_2$—$CH_2$— | $CH_3$ | $CH_3$ | 6-$CH_3$ | $C_2H_5$— | |
| 125 | —$SO_2$—$CH_2$— | $CH_3$ | $CH_3$ | 6-$CH_3$ | $(CH_3)_2CH$— | |
| 126 | —$CH_2$—S— | $CH_3$ | $CH_3$ | 6-$CH_3$ | $C_2H_5$— | |
| 127 | —$CH_2$—S— | $CH_3$ | $CH_3$ | 6-$CH_3$ | $(CH_3)_2CH$— | |
| 128 | —$CH_2$—SO— | $CH_3$ | $CH_3$ | 6-$CH_3$ | $C_2H_5$— | |
| 129 | —$CH_2$—$SO_2$— | $CH_3$ | $CH_3$ | 6-$CH_3$ | $C_2H_5$— | |

TABLE 3-continued (Ic)

$$R^2-O-\overset{O}{\underset{\|}{C}}-O-\text{[structure with A-B, X, Y, Z}_n\text{]}$$

| No. | A—B | X | Y | $Z_n$ | $R^2$ | m.p. °C. |
|---|---|---|---|---|---|---|
| 130 | —S—CH$_2$— | CH$_3$ | CH$_3$ | 6-CH$_3$ | C$_2$H$_5$— | oil |
| 131 | —S—CH$_2$ | CH$_3$ | CH$_3$ | 6-CH$_3$ | (CH$_3$)$_2$CH— | oil |

INTERMEDIATES

Example I

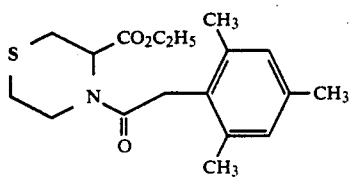

175.3 g (1 mol) of ethyl thiomorpholine-3-carboxylate are dissolved in 1000 ml of abs. THF, 140 ml (1 mol) of triethylamine are added and 198.5 g (1 mol) of mesitylene acetyl chloride are added dropwise at 0° to 10° C. The mixture is subsequently stirred at room temperature for a further 1 h and poured into 4.5 l of ice water and 500 ml of 1 N HCl, and a flocculant, strongly water-containing product is filtered off with suction, taken up in methylene chloride, dried using MgSO$_4$ and concentrated on a rotary evaporator. In this manner, 317.2 g (=94.7% of theory) of ethyl N-(2,4,6-trimethylphenyl-acetyl)-thiomorpholine-3-carboxylate are obtained as a pale yellow oil.

$^1$H-NMR (200 MHz, CDCl$_3$); δ=1.25 (t, 3 H,CH$_{2CH3}$), 2.18 (s, 6 H, AR—2—CH$_3$, Ar—6—CH$_3$), 2.21 (s, 3 H, Ar—4—CH$_3$), 4.2 (q, 2 H, —CH$_2$—CH$_3$), 5.68 ("t", 1 H,

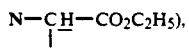

6.8 (s, 2 H, Ar—3—H, Ar—5—H).

The active compounds are suitable for combating animal pests, preferably arthropods and nematodes, in particular insects and arachnida, which are encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.* From the order of the Dermaptera, for example, *Forficula auricularia.* From the order of the Isoptera, for example, *Reticulitermes spp..* From the order of the Anoplura, for example, *Phylloxera vastatrix, Pemphigus spp., Pediculus humanus corporis, Haematopinus spp.* and *Linognathus spp.* From the order of the Mallophaga, for example, *Trichodectes spp.* and *Damalinea spp.* From the order of the Thysanoptera, for example, *Hercinothrips femoralis* and *Thrips tabaci.* From the order of the Heteroptera, for example, *Eurygaster spp., Dysdercus intermedius, Piesma quadrata, Cimex lectularius, Rhodnius prolixus* and *Triatoma spp.* From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.* From the order of the Lepidoptera, for example, *Pectinophora gossypiella, Bupalus piniiarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp.. Earias insulana, Heliothis spp., Spodoptera exigua, Mamestra brassicae, Panolis flammea, Prodenia litura, Spodoptera spp., Trichoplusia ni, Caprocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lycrus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Cosrelyrra zealandica.* From the order of the Hymenoptera, for example, *Diprion spp., Hoplocampa spp., Lasius spp., Monomorium pharaonis* and *Vespa spp.* From the order of the Diptera, for example, *Aedes spp., Anopheles spp., Culex spp., Drosoph-*

*ila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa*. From the order of the Siphonaptera, for example, *Xenopsylla cheopis* and *Ceratophyllus spp*. From the order of the Arachnida, for examle, *Scorpio maurus* and *Latrodectus mactans*. From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The phytoparasitic nematodes include *Pratylenchus spp., Radopholus similis, Ditylenchus dipsaci, Tylenchulus semipenetrans, Heterodera spp., Globodera ssp., Meloidogyne spp., Aphelenchoides spp., Longidorus spp., Xiphinema spp.* and *Trichodorus spp.*.

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

It is characteristic of the compounds according to the invention that they have a selective activity against monocotyledon weeds in monocotyledon and dicotyledon cultures in the pre- and post-emergence method together with good tolerability for cultivated plants.

The active compounds according to the invention can be used, for example, in connection with the following plants:

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In addition to an outstanding action against harmful plants, the active compounds according to the invention at the same time show good tolerability towards important cultivated plants, such as, for example, wheat, cotton, soy beans, citrus fruit and sugar beets, and can therefore be employed as selective weed control agents.

The active compounds can be converted into the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, herbicides or fungicides. The insecticides include, for example, phosphates, carbamates, carboxylates, chlorinated hydrocarbons, phenylureas and substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

For example, the active compounds can be used as such, in the form of their formulations or the use forms prepared therefrom by further dilution or by combination with emulsifiable oils, surface-active substances and other additions, such as ready-to-use solutions, suspensions, emulsions, powders, pastes and granules. They are used in the customary manner, for example by watering, spraying, atomizing or scattering.

The active compounds according to the invention can be applied as herbicides both before and after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.01 and 5 kg per ha.

The active compounds which can be used according to the invention are also suitable for combating midges, ticks, etc., in the field of animal keeping and cattle breeding, it being possible to achieve better results, for example higher milk yields, greater weight, more attractive animal pelt, longer lifetime, etc., by combating the pests.

The active compounds which can be used according to the invention are administered in this field in a known manner such as by oral administration in the form of, for example, tablets, capsules, drinks, granules, by dermal or external use in the form, for example, of dipping, spraying, pouring-on and spotting-on and powdering in and also by parenteral administration in the form, for example, of injection and furthermore by the "feed-through" method. Administration is also possible as molded articles (collar, ear tag).

The use of the active compounds according to the invention can be seen from the following examples.

EXAMPLE A

Tetranychus test (resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Phaseolus vulgaris) which are heavily infested with the common spider mite or two-spotted spider mite (Tetranychus urticae) in all stages of development are treated by being dipped into the preparation of the active compound of the desired concentration.

After the specified period of time, the destruction in % is determined. 100% means that all the spider mites have been killed; 0% means that none of the spider mites have been killed.

In this test, for example, the compounds of the Preparation Examples show superior activity compared to the prior art.

EXAMPLE B

Nephotettix test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the active compound preparation of the desired concentration and are infested with larvae of the green rice leafhopper (*Nephotettix cincticeps*) for as long as the seedlings are still moist.

After the specified period of time, the destruction in % is determined. 100% means that all the leaf-hoppers have been killed; 0% means that none of the leafhoppers have been killed.

In this test, for example, the compounds of the Preparation Examples show superior activity compared to the prior art.

EXAMPLE C

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no imporatnce, only the amount of active compound applied per unit area being decisive. After three weeks, the degree of damage to the plants is rated in % damage in comparison to the development of the untreated control. The figures denote:

In this test, for example, the compounds of the Preparation Examples show superior activity compared to the prior art.

EXAMPLE D

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

In this test, for example, the compounds of the Preparation Examples show superior activity compared to the prior art.

It will be understood that the specification and examples are illustrative but not limitative of the present invention and that other embodiments within the spirit and scope of the invention will suggest themselves to those skilled in the art.

We claim:

1. A 3-phenyl derivative of the formula

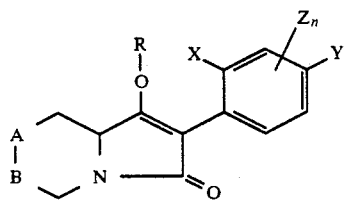

(I)

in which

A—B represents —S—$CH_2$—, —SO—$CH_2$—, —$SO_2$—$CH_2$—, —$CH_2$—S—, —$CH_2$—SO or —$CH_2$—$SO_2$—, X represents $C_1$-$C_6$-alkyl, halogen or $C_1$-$C_6$-alkoxy, Y represents hydrogen, $C_1$-$C_6$-alkyl, halogen, $C_1$-$C_6$-alkoxy or $C_1$-$C_3$-halogenoalkyl, Z represents $C_1$-$C_6$-alkyl, halogen or $C_1$-$C_6$-alkoxy, n represents a number from 0-3, R represents hydrogen, or a group of the formula

—CO—$R^1$,

—CO—O—$R^2$ or

E, in which

E represents a metal cation equivalent or an ammonium ion, $R^1$ represents $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, $C_1$-$C_8$-polyalkoxy-$C_2$-$C_8$-alkyl or cycloalkyl having 5-6 ring atoms, which may be interrupted by oxygen or sulphur, and which are optionally substituted by halogen, represents phenyl which is optionally substituted by halogen, nitro, $C_1$-$C_6$-alkyl, $C_1$-$C_6$-alkoxy, $C_1$-$C_6$-halogenoalkyl or $C_1$-$C_6$-halogenoalkoxy, represents phenyl-$C_1$-$C_6$-alkyl which is optionally substituted by halogen, $C_1$-$C_6$-alkyl, $C_1$-$C_6$-alkoxy, $C_1$-$C_6$-halogenoalkyl or $C_1$-$C_6$-halogenoalkoxy, represents pyridyl, pyrimidyl, thiazolyl or pyrazolyl optionally substituted by halogen or $C_1$-$C_6$-alkyl, represents phenoxy-$C_1$-$C_6$-alkyl optionally substituted by halogen or $C_1$-$C_6$-alkyl, or represents pyridyloxy-$C_1$-$C_6$ alkyl, pyrimidyloxy-$C_1$-$C_6$-alkyl or thiazolyloxy-$C_1$-$C_6$ alkyl optionally substituted by halogen, amino or $C_1$-$C_6$-alkyl, and $R^2$ represents $C_1$-$C_{20}$-alkyl, $C_2$-$C_{20}$-alkenyl, $C_1$-$C_8$-alkoxy-$C_2$-$C_8$-alkyl or $C_1$-$C_8$-polyalkoxy-$C_2$-$C_8$-alkyl which are optionally substituted by halogen, or represents phenyl optionally substituted by halogen, nitro, $C_1$-$C_6$-alkyl, $C_1$-$C_6$-alkoxy or $C_1$-$C_6$-halogenoalkyl.

2. A 3-phenyl derivative according to claim 1, in which

A—B represents —S—$CH_2$—, —SO—$CH_2$—, —$SO_2$—$CH_2$—, —$CH_2$—S—, —$CH_2$—SO or —$CH_2$—$SO_2$—, X represents $C_1$-$C_4$-alkyl, halogen or $C_1$-$C_4$-alkoxy, Y represents hydrogen, $C_1$-$C_6$-alkyl, halogen, $C_1$-$C_4$-alkoxy or $C_1$-$C_2$-halogenoalkyl, Z represents $C_1$-$C_4$-alkyl, halogen or $C_1$-$C_4$-alkoxy, n represents a number from 0-3, R represents hydrogen, or a group of the formula

—CO—$R^1$,

—CO—O—$R^2$ or

E, in which

E represents a metal cation equivalent or an ammonium ion, $R^1$ represents $C_1$-$C_{16}$-alkyl, $C_2$-$C_{16}$-alkenyl, $C_1$-$C_6$-alkoxy-$C_1$-$C_6$-alkyl, $C_1$-$C_6$-alkylthio-$C_1$-$C_6$-alkyl, $C_1$-$C_6$-polyalkoxy-$C_2$-$C_6$-alkyl or cycloalkyl having 5-6 ring atoms, which can be interrupted by 1-2 oxygen or sulphur atoms, and which is optionally substituted by halogen, represents phenyl optionally substituted by halogen, nitro, $C_1$-$C_4$-alkyl, $C_1$-$C_4$-alkoxy, $C_1$-$C_3$-halogenoalkyl or $C_1$-$C_3$-halogenoalkoxy, represents phenyl-$C_1$-$C_4$-alkyl optionally substituted by halogen, $C_1$-$C_4$-alkyl, $C_1$-$C_4$-alkoxy, $C_1$-$C_3$-halogenoalkyl or $C_1$-$C_3$-halogenoalkoxy, represents pyridyl, pyrimidyl, thiazolyl or pyrazolyl optionally substituted by halogen or $C_1$-$C_6$-alkyl, optionally represents phenoxy-$C_1$-$C_5$-alkyl substituted by halogen or $C_1$-$C_4$-alkyl, or represents pyridyloxy-$C_1$-$C_5$ alkyl, pyrimidyloxy-$C_1$-$C_5$-alkyl or thiazolyloxy-$C_1$-$C_5$ alkyl optionally substituted by halogen, amino or $C_1$-$C_4$-alkyl, $R^2$ represents $C_1$-$C_{16}$-alkyl, $C_2$-$C_{16}$-alkenyl, $C_1$-$C_{16}$-alkoxy-$C_2$-$C_6$-alkyl or $C_1$-$C_6$-polyalkoxy-$C_2$-$C_6$-alkyl which are optionally substituted by halogen, or represents phenyl optionally substituted by halogen, nitro, $C_1$-$C_4$-alkyl, $C_1$-$C_3$-alkoxy or $C_1$-$C_3$-halogenoalkyl.

3. A 3-phenyl according to claim 1, in which

A—B represents —S—$CH_2$—, —SO—$CH_2$—, —$SO_2$—$CH_2$—, —$CH_2$—S—, —$CH_2$—SO—, or —$CH_2SO_2$—, X represents methyl, ethyl, propyl, i-propyl, fluorine, chlorine, bromine, methoxy or ethoxy, Y represents hydrogen, methyl, ethyl, propyl, i-propyl, butyl, i-butyl, tert.-butyl, chlorine, bromine, methoxy, ethoxy or trifluoromethyl, Z represents methyl, ethyl, i-propyl, butyl, i-butyl, tert.-butyl, chlorine, bromine, methoxy or ethoxy, n represents a number from 0-3, R represents hydrogen, or a group of the formula

—CO—$R^1$,

—CO—O—$R^2$ or

E, in which

E represents a metal cation equivalent or an ammonium ion, $R^1$ represents $C_1$-$C_{14}$-alkyl, $C_2$-$C_{14}$-alkenyl, $C_1$-$C_4$-alkoxy-$C_1$-$C_6$-alkyl, $C_1$-$C_4$-alkylthio-$C_1$-$C_6$-alkyl, $C_1$-$C_4$-polyalkoxyl-$C_2$-$C_4$-alkyl or cycloalkyl having 5-6 ring atoms, which can be interrupted by 1-2 oxygen or sulphur atoms, and which are optionally substituted by fluorine or chlorine, represents phenyl optionally substituted by fluorine, chlorine, bromine, methyl, ethyl, propyl, i-propyl, methoxy, ethoxy, trifluoromethyl, trifluoromethoxy or nitro, represents phenyl-$C_1$-$C_3$-alkyl optionally substituted by fluorine, chlorine, bromine, methyl, ethyl, propyl, i-propyl, methoxy, ethoxy, trifluoromethyl or trifluoromethoxy, represents pyridyl, pyrimidyl, thiazolyl or pyrazolyl which are optionally substituted by fluorine, chlorine, bromine, methyl or ethyl, represents phenoxy-$C_1$-$C_4$-alkyl optionally substituted by fluorine, chlorine, methyl or ethyl, or represents pyridyloxy-$C_1$-$C_4$-alkyl, pyrimidyloxy-$C_1$-$C_4$-alkyl or thiazolyloxy-$C_1$-$C_4$-alkyl which are optionally substituted by fluorine, chlorine, amino, methyl or ethyl, $R^2$ represents $C_1$-$C_{14}$-alkyl, $C_2$-$C_{14}$-alkenyl, $C_1$-$C_4$-alkoxy-$C_2$-$C_6$-alkyl or $C_1$-$C_4$-polyalkoxy-$C_2$-$C_6$-alkyl which are optionally substituted by fluorine or chlorine, or represents phenyl optionally substituted by fluorine, chlorine, nitro, methyl, ethyl, propyl, i-propyl, methoxy, ethoxy or trifluoromethyl.

4. A 3-phenyl according to claim 1, in which

A—B represents —S—$CH_2$—, —SO—$CH_2$—, —$SO_2$—$CH_2$—, —$CH_2$—S—, —$CH_2$—SO— or —$CH_2SO_2$.

5. A pesticidal composition comprising a pesticidally effective amount of a compound according to claim 1 and a diluent.

6. A method of combating pests which comprises applying to such pests or to a locus from which it is desired to exclude such pests a pesticidally effective amount of a compound according to claim 1.

* * * * *

UNITED STATES PATENT AND TRADEMARK OFFICE
CERTIFICATE OF CORRECTION

PATENT NO. : 5,116,836

DATED : May 26, 1992

INVENTOR(S) : Fischer et al.

It is certified that error appears in the above-identified patent and that said Letters Patent is hereby corrected as shown below:

Col. 29, line 37    After " 3-phenyl " insert -- -pyrrolidine-2,4-dione --

Col. 30, line 27    After " 3-phenyl " insert -- -pyrrolidine-2,4-dione --

Col. 31, line 7     After " 3-phenyl " insert -- -pyrrolidine-2,4-dione --

Col. 31, line 9     After " SO- " delete " , "

Col. 32, line 25    After " 3-phenyl " insert -- -pyrrolidine-2,4-dione --

Signed and Sealed this

Ninth Day of November, 1993

Attest:

BRUCE LEHMAN

*Attesting Officer*         *Commissioner of Patents and Trademarks*